(12) United States Patent
Chevalier et al.

(10) Patent No.: US 6,780,471 B2
(45) Date of Patent: Aug. 24, 2004

(54) CURABLE SILICONE RESIN COMPOSITION AND REACTIVE SILICON COMPOUNDS

(75) Inventors: Pierre Chevalier, Penarth (GB); Iain A MacKinnon, Sully (GB); Bizhong Zhu, Midland, MI (US); Robert Jean-Pierre Corriu, Montpellier (FR); Genevieve Marie-Louise Emile Cerveau, Montpellier (FR); Bertrand Francois Dabiens, Montpellier (FR)

(73) Assignee: Dow Corning Corporation, Midland, MI (US)

( * ) Notice: Subject to any disclaimer, the term of this patent is extended or adjusted under 35 U.S.C. 154(b) by 0 days.

(21) Appl. No.: 10/258,722

(22) PCT Filed: Apr. 24, 2001

(86) PCT No.: PCT/EP01/04606

§ 371 (c)(1),
(2), (4) Date: Dec. 13, 2002

(87) PCT Pub. No.: WO01/83608

PCT Pub. Date: Nov. 8, 2001

(65) Prior Publication Data

US 2003/0130389 A1 Jul. 10, 2003

(30) Foreign Application Priority Data

Apr. 27, 2000 (EP) .......................................... 00401160

(51) Int. Cl.$^7$ ................................................ B05D 3/10
(52) U.S. Cl. ......................... 427/387; 528/35; 528/43; 525/477
(58) Field of Search ..................... 528/43, 35; 525/477; 427/387

(56) References Cited

U.S. PATENT DOCUMENTS

| | | | |
|---|---|---|---|
| 3,464,937 A | 9/1969 | Bamford et al. | ............... 260/18 |
| 5,034,061 A | 7/1991 | Maguire et al. | ....... 106/287.14 |
| 5,747,608 A | 5/1998 | Katsoulis et al. | ........... 525/477 |
| 5,830,950 A | 11/1998 | Katsoulis et al. | ........... 525/477 |

FOREIGN PATENT DOCUMENTS

| | | | |
|---|---|---|---|
| CA | 691206 | 7/1964 | ................. 400/73 |
| GB | 1101589 | 1/1968 | ........... C08G/47/00 |
| GB | 1119666 | 10/1968 | ........... C08G/31/00 |

OTHER PUBLICATIONS

Boury et al., Chem. Mater., 11 (1999) 2796–2803.*
Corriu R. et al; Chem. Mater. (1992) 4, pp. 1217–1224.
Corriu R. et al: Chem. Comm, (1996), 15, pp. 1845–1846.
Shea, K.J. et al:, J. Am. Chem. Soc. 114 (17) (1992) p. 6700.
Loy, D.A. et al: "Bridged Polysilsesquioxanes. Highly porous hybrid organic–inorganic materials", Chem. Rev. 1995,95, pp. 1431–1442.
Dvornic P.R. et al: "Exactly alternating silarylene–siloxane polymers: 9. Relationships between polymer structure and glass transition temperature", Macromolecules, vol. 25, No.14, Jul. 6, 1992, pp. 3769–3778.
Corriu R. et al; "Thermal isomerisation of alternating silphenylene–siloxane copolymer", J.Polymer Science, vol. 32, No. 1, Jan. 15, 1994, pp. 187–191.
Dvornic P.R. et al: "Exactly alternating silarylene–siloxane polymers: 10. Synthesis and characterisation of silphenylene–siloxane polymers containing fluoroalkyl and hydrido side groups", Macromolecules, vol. 27, No. 20,26.
Cerveau G. et al: "Sol–gel process: temperature effect on textural properties of a monophasic hybrid material", Chem. Commun., Jul. 26, 1999, pp. 2081–2082.

* cited by examiner

*Primary Examiner*—Kuo-Liang Peng
(74) *Attorney, Agent, or Firm*—Patricia M. Scaduto (57) ABSTRACT

A curable silicone resin composition comprises (A) an uncured silicone resin having units of the formula $(R^*)_a(R)_b SiO_{(4-a-b)/2}$, where each R* is a functional group capable of reacting with Si—OH and/or Si-alkoxy groups and each R is a nonfunctional monovalent hydrocarbon group, a+b is from 1.0 to 3.0 and each molecule of uncured silicone resin contains an average of at least two groups R*, and (B) a silanol or hydrolysable compound of the formula (I) where R' represents a hydroxyl group or a hydrolysable group; each R" represents hydrogen, a monovalent hydrocarbon which optionally is substituted, or a group within the above definition of R'; and Ar is a substantially nonflexible linkage including at least one para-arylene moiety, so that the groups $(R')_2R"Si—$ are spatially separated.

21 Claims, 2 Drawing Sheets

CURABLE SILICONE RESIN COMPOSITION AND REACTIVE SILICON COMPOUNDS

CROSS REFERENCES TO RELATED APPLICATIONS

The present application is a US national stage filing under 35 USC 371 and claims priority from PCT Application No. PCT/EP01/04606 entitled "CURABLE SILICONE RESIN COMPOSITION AND REACTIVE SILICON COMPOUNDS," filed on Apr. 24, 2001, currently pending, which claims priority from EP 00401160.7, also entitled "CURABLE SILICONE RESIN COMPOSITION AND REACTIVE SILICON COMPOUNDS," filed on Apr. 27, 2000. The above identified applications are incorporated by reference in their entirety.

FIELD OF THE INVENTION

This invention relates to curable silicone resin compositions and to reactive silicon compounds useful in such curable compositions.

BACKGROUND OF THE INVENTION

Curable silicone resins such as silsesquioxane resins are used in applications which take advantage of their heat and fire resistant properties, for example in fibre reinforced composites for electrical laminates and structural components for automotive, aircraft and naval use, and as interlayer dielectric materials and as abrasion resistant coatings. The resins cure to a rigid product. There is a need for silicone resin compositions of improved mechanical properties, such as increased flexural strength, fracture toughness, modulus and/or mechanical damping, without substantial loss of heat and fire resistance.

The toughness of a silicone resin has been increased by a rubber component, as described in U.S. Pat. No. 5,747,608 or U.S. Pat. No. 5,830,950 or by a silicone fluid as described in U.S. Pat. No. 5,034,061 or CA 691206.

GB 1119666 describes a resinous polymer comprising the reaction product of a compound of the formula $(R)_n(X)_{(3-n)}Si—R"—Si(X)_{(3-n)}(R)_n$, wherein R is a monovalent hydrocarbon group, R' is phenylene, diphenylene or diphenylene oxide, X is hydroxy or alkoxy and n is 1 or 2 and a silane of the general formula $(R")_mSi(Y)_{4-m}$, wherein R" is a hydrocarbyl or substituted hydrocarbyl group, Y is alkoxy, acyloxy or hydroxy and m=0–2. GB1101589 describes a process for the production of an organosilicon resin by heating in the presence of a solvent a compound of the formula $R1(R2)_2Si—R—Si(R2)_2R1$ where R is phenylene, diphenylene or diphenylene oxide, R1 is a monovalent hydrocarbon or substituted hydrocarbon group and R2 is alkoxy or hydroxy, with a compound of the formula $R4(R3)_2Si—R—Si(R3)_2R4$ where each R3 is a monovalent hydrocarbon or substituted hydrocarbon group and R4 is acyloxy, alkoxy or hydroxy.

SUMMARY OF THE INVENTION

A curable silicone resin composition according to the present invention comprises (A) an uncured silicone resin having units of the formula $(R^*)_a(R)_bSiO_{(4-a-b)/2}$, where each $R^*$ is a functional group capable of reacting with Si—OH and/or Si-alkoxy groups and each R is a nonfunctional monovalent hydrocarbon group, a+b is from 1.0 to 3.0 and each molecule of uncured silicone resin contains an average of at least two groups $R^*$, and (B) a silanol or hydrolysable compound of the formula where each R' represents a hydroxyl group or a hydrolysable group; each R" represents hydrogen, a monovalent hydrocarbon which optionally is substituted, or a group within the above definition of R'; and Ar is a substantially nonflexible linkage including at least one para-arylene moiety, so that the groups (R')₂R"Si— are spatially separated.

The compound (B) reacts with the functional groups $R^*$ of the silicone resin to crosslink the resin (A) to a structure having improved mechanical properties and generally less brittle than that obtained by curing the resin (A) alone. The groups (R')₂R"Si— are spatially separated by the nonflexible linkage Ar so that intramolecular self-reaction of the groups (R')₂R"Si— is avoided.

DETAILED DESCRIPTION OF THE INVENTION

The nonflexible linkage Ar can be a simple p-phenylene moiety or can contain two or more phenylene groups linked in an array in such a way that the array is held in a substantially linear conformation, that is the linkage between the phenylene groups does not contain any atoms about which the parts of the molecule can freely rotate, such as a carbon atom positioned between two C—C single bonds. The p-phenylene groups can be part of a fused ring system such as a 1,4-naphthylene or 1,10-anthracene linkage, and the term "para-arylene moiety" includes other fused ring aromatic linkages in which the (R')₂R"Si— groups are maintained spatially separated such as a 1,5- or 2,6-naphthylene linkage or even a metallocene, e.g. ferrocene linkage in which the (R')₂R"Si— groups are bonded to different cyclopentadiene rings.

The compounds (B) in which the group R" is a hydroxyl group and Ar contains two or more phenylene groups per molecule are new compounds. The invention thus includes an organosilicon compound of the formula (HO)₃Si—Ar'—Si(OH)₃ wherein Ar' is a linkage containing two or more phenylene moieties held in a substantially linear conformation so that the (R')₃Si— groups are spatially separated.

All the compounds (B) in which Ar comprises two or more para-arylene moieties joined by an organic linkage which does not allow free rotation are new compounds. The invention thus includes an organosilicon compound of the formula wherein R' and R" are defined as in claim 1, each Ap is a para-arylene moiety, and X is a substantially inflexible linkage having at least two carbon atoms so that the groups (R')₂R"Si— are spatially separated.

The structure of the linkage X is such that in combination with the adjacent phenylene groups there is provided a substantially linear rigid-rod array. It is preferred that there are from 2 to 4 phenylene groups, more preferably only 2 phenylene groups, per molecule. Preferably X comprises a direct bond or a linkage comprising a carbon—carbon double bond, for example vinylene —CH=CH—, or one or two carbon—carbon triple bonds, for example an acetylene or butadiyne linkage. Where X comprises a C=C double bond, the phenylene groups are generally positioned trans- to one another; although this arrangement is not strictly linear, it holds the para-(hydroxysilyl) subtituents on the phenylene groups apart from each other and is "substantially linear" within the terms of this invention.

The para-phenylene groups Ph or any phenylene group within linkage Ar can be substituted by one or more alkyl, for example methyl, ethyl, butyl, hexyl or dodecyl, aryl, aralkyl or alkenyl group, although the phenylene groups are preferably unsubstituted.

Examples of preferred organobis(silane triol)s according to the invention include 4,4'-bis(trihydroxysilyl)biphenyl,
4,4'-bis(trihydroxysilyl)stilbene,
bis(4-trihydroxysilylphenyl)acetylene and
1,4-bis(4-trihydroxysilylphenyl)butadiyne.

The organobis(silane triol)s of the invention can be prepared by, for example, the hydrolysis of corresponding organobis(trialkoxysilyl) and organobis(trichlorosilyl) compounds. An organobis(trialkoxysilyl) precursor can for example be hydrolysed by the methods described by Hyde as disclosed in J.Am.Chem.Soc. 1953, 75, at page 2166 or Tyler as disclosed in J.Am.Chem.Soc. 1955, 77, at page 770.

Examples of organobis(trialkoxysilyl) compounds which can be used as compound (B) include 4,4'-bis(trimethoxysilyl)biphenyl,
4,4'-bis(trimethoxysilyl)stilbene,
bis(4-trimethoxysilylphenyl)acetylene and
1,4-bis(4-trimethoxysilylphenyl)butadiyne Bis(trimethoxysilylphenyl)-substituted acetylenic compounds can be prepared from the condensation reaction of para-bromo(trimethoxysilyl) benzene or para-iodo (trimethoxysilyl) benzene with para-(trimethoxysilyl) phenylacetylene. Bis(trimethoxysilyl) substituted diphenylbutadiynes can be prepared by the homo coupling reaction of para-(trimethoxysilyl)phenylacetylene.

Hydrolysis can take place under mild conditions, even by the use of water alone, although it is preferred that a catalyst such as an organic acid, particularly acetic acid, is present in order to facilitate the hydrolysis reaction. It is preferred that from 0.1 to 5% by weight of catalyst based on the weight of water present is used in the reaction mixture, more preferably from 0.25 to 2%.

The relative proportions of water and organobis (trialkoxysilyl) precursor may vary between wide limits. Generally at least 6 moles water is present per mole of organobis(trialkoxysilane) and sufficient water may be used for the bis(trihydroxysilyl)arene product to dissolve in the aqueous phase.

The hydrolysis of the organobis(trialkoxysilane) is preferably carried out in the presence of solvent, most preferably a dipolar aprotic organic solvent such as diethyl ether or dichloromethane. The reaction temperature is preferably in the range from 0° C. to 40° C., for example ambient temperatures. The water and catalyst may be incorporated separately into the reaction mixture or can be pre-mixed prior to addition to the organobis(trialkoxysilyl) precursor. The reaction period for the hydrolysis to reach completion (i.e. the hydrolysis of all the alkoxy groups present on the organobis(trialkoxysilyl) precursor) is generally from about 30 minutes up to 1 month and the preferred reaction period is from about 1 hour to about 4 days, most preferably from 4 to 24 hours.

Upon completion of the hydrolysis reaction, the organobis (silane triol) may be recovered from the reaction mixture by conventional means, for example, by filtration or evaporation.

In a preferred procedure organobis(trialkoxysilane) in ether is added drop-wise quickly to a 0.5% acetic acid/water solution at 20° C. The mixture is then stirred thoroughly until the resulting organobis(silane triol) precipitates out in the aqueous phase. After filtration and drying overnight at 25° C. the organobis(silane triol) is recovered.

An alternative method of making the organobis(silane triol) is from a organobis(trichlorosilyl) precursor. This method includes the hydrolysis reaction of an organobis (trichlorosilyl) compound with a water/aniline mixture to form the organobis(silane triol). The reaction is based on the method of Takiguchi as disclosed in J.Am.Chem.Soc. 1959, 81, at page 2359. Organobis(trichlorosilane) can be dissolved in dry diethyl ether and added drop-wise to an emulsion of a stoichiometric amount of water and aniline at a temperature of 0° C. After removal of anilinium salts by filtration from the reaction mixture, organobis(silane triol) is recovered. The bis((hydrocarbyldihydroxysilyl)phenyl) compounds, that is those compounds (B) in which R" is a monovalent hydrocarbon group, can be prepared by analogous procedures. For example bis(4-(methyldimethoxysilyl) phenyl)acetylene can be prepared by condensation of para-bromo(methyldimethoxysilyl)benzene with para-(methyldimethoxysilyl)phenylacetylene and can be hydrolysed to bis(4-(methyldihydroxysilyl)phenyl) acetylene by the procedures described above.

The compounds (B) according to this invention are effective in crosslinking the silicone resin (A) and have high stability against intramolecular self-condensation. The invention thus includes a process for forming a cured resin composition comprising mixing (A) and (B) and curing the resulting composition under conditions such that (A) and (B) are copolymerised.

(A) is an uncured silicone resin having units of the formula $(R^*)_a(R)_bSiO_{(4-a-b)/2}$, where each R* is a functional group capable of reacting with Si—OH and/or Si-alkoxy groups and each R is a nonfunctional monovalent hydrocarbon group and a+b is from 1.0 to 3.0. Each molecule of uncured silicone resin contains an average of at least two groups R*. The groups R* can be —OH groups, alkoxy groups or H atoms bonded to Si. Typically, R is selected from alkyl and aryl groups. Suitable alkyl groups include methyl, ethyl, isopropyl, n-butyl and isobutyl. Suitable aryl groups are exemplified by phenyl. Organosilicone resins, particularly those prepared by acid hydrolysis and condensation, generally include a considerable concentration of residual hydroxyl groups which can react with the hydroxysilyl or alkoxysilyl groups of the compound (B) through a condensation cure system.

The amount of (A) in the curable system is generally 5 to 96%, preferably 50 to 95%, by weight. Most preferably, the weight ratio of (A) to (B) is 5:1 to 20:1.

The curable silicone resin composition of the invention preferably contains a catalyst so that condensation curing can be carried out at reduced, e.g. ambient temperature. The catalyst can be a metal ester or alkoxide of a Group IVB metal such as zirconium, hafnium or titanium, for example titanium tetrabutoxide, a metal carboxylate such as zinc octoate, choline octoate, a strong acid such as sulphuric or phosphoric acid or a base such as KOH, CsOH, a metal silanolate, calcined lime or an amine or quaternary base, for example tetramethyl ammonium hydroxide. The catalyst can generally be used at up to 2% by weight based on reagents, preferably 0.02 to 0.4%.

The curable composition may additionally contain a silicone rubber, for example a rubber as described in U.S. Pat. No. 5,747,608 or U.S. Pat. No. 5,830,950. The rubber generally has terminal functional groups capable of reacting with the hydroxyl groups of silicone resin (A). The silicone rubber, if used, can be present at up to 30% by weight, for example 5 to 20%.

The curable composition can optionally contain a solvent at up to 90%, preferably up to 60% of the composition. For example a substrate having a cure silicone resin coated thereon can be prepared by mixing (A) and (B) in a solvent, coating the resulting solution on the substrate, and drying the coating and subjecting it to curing conditions. A moulded cured silicone resin can be produced by mixing (A) and (B) in a solvent, casting the resulting solution in a mould, removing the solvent and curing the composition in the mould. The solvent is generally a polar organic solvent, for example an amide such as formamide, dimethylformamide or dimethylacetamide, a halogenated hydrocarbon such as dichloromethane or 1,1,1-trichloroethane, an alcohol such as methanol, ethanol, isopropanol or t-butanol, an aromatic hydrocarbon such as toluene or xylene, a glycol ether such as 2-methoxypropanol, 2-butoxypropanol, butoxyethanol or dipropylene glycol methyl ether, or a sulphoxide such as dimethyl sulphoxide. The more polar solvents such as alcohols, formamide or dimethyl sulphoxide may be required to dissolve the organobis(silanetriol)s.

The curable composition can be coated on a substrate, for example as a solution, and cured to form a thin film on the substrate, or can be cured in a mould to form a shaped silicone resin article.

The novel compounds of the formula (R')$_3$Si—Ar'—Si(R')$_3$ can also be cured alone to produce strong solid resins by condensation of the R' groups. If curing is carried out in a solvent such as formamide, a gel is produced which can be powdered and dried to recover the solid resin, which contains extended chains containing arylene linkages and silicate crosslinks.

The compounds (B), particularly the bis(trihydroxysilyl)arene compounds and the bis(dihydroxysilyl)arene compounds, have X-ray patterns showing that they are ordered in the solid state. It is believed that resins formed by polymerisation of the bis(trihydroxysilyl)arene compounds are also ordered in the solid state, and that the cured compositions of the invention formed from a silicone resin and compound (B) also show ordering in the solid state. These polymers and cured resin compositions thereby give optical effects which can be utilised in electro-optic products.

There now follows a number of examples in which all parts and percentages are given by weight unless otherwise indicated.

EXAMPLE 1

Preparation of 4,4'-Bis(trihydroxysilyl)biphenyl

To a flask fitted with a dropping funnel, mechanical stirrer and temperature probe was added a solution of 4,4'-bis(trimethoxysilyl)biphenyl (1 g, 2.53 mmol., prepared as described by Corriu et al., Chem. Mater. (1992) 4, 1217–1224) in ether (3 ml) at a temperature of 20° C. The dropping funnel was charged with a 0.5% acetic acid solution (1.10 ml) The acetic acid solution was quickly added dropwise to the flask and the reaction mixture separated into two phases. The white biphasic mixture was well agitated for a period of twenty-four hours at a temperature of 20° C. During this period, a colourless solid precipitated out in the aqueous phase. The reaction mixture was filtered and the recovered precipitate was washed three times each with ethanol, acetone and ether and then dried overnight at a temperature of 20° C. to give a white crystalline solid.

$^1$H NMR (DMSO-d6) analysis of the solid gave two signals at 7.69 (4H, d), 7.63 (4H, d) and 6.43 ppm (6H, s) representing the aryl protons of phenyl groups and hydroxyl groups respectively and indicated the conservation of the molecular structure of the precursor, 4,4'-bis(trimethoxysilyl)biphenyl and the presence of 6 hydroxyl groups. $^{13}$C NMR (DMSO-d6) analysis gave 4 signals at 141.2, 136.8, 135.5 and 126.3 ppm corresponding to the 4 aromatic carbon atoms of the phenyl groups and there was no signal present for the methoxy group of the pre-cursor. $^{29}$Si NMR gave a singlet at −54.3 ppm corresponding to a silanetriol unit. Fourier Transform Infrared (FTIR) spectrum gave a strong broad band at 3219 cm$^{-1}$ attributable to OH stretching frequencies involved in hydrogen bonding. Analysis by $^1$H, $^{13}$C and $^{29}$Si NMR and FTIR identified the solid as 4,4'-bis(trihydroxysilyl)biphenyl obtained at a 95% yield. Anal. Calc.; for $C_{12}H_{14}O_6Si_2$: C, 46.44; H, 4.54; Si, 18.09%. Found; C, 45.44; H, 4.70; Si, 18.20%.

EXAMPLE 2

4,4'-bis-(trimethoxysilyl)stilbene was prepared as follows:

A solution of 4-(trimethoxysilyl)styrene (1.5 g, 6.7 mmol, prepared as described by Corriu et al., Chem. Comm, (1996), 15, 1845–1846) and 4-bromo(1-trimethoxysilyl)benzene were dissolved in dry toluene (15 ml). Palladium acetate (10 mg, 4.45 10$^{-5}$ mol), dry triethylamine (1.35 g, 13.3 mmol) and tri-orthotolylphosphine (TOP) (0.08 g, 2.67 10$^{-5}$ mol) were added all at once successively (following the Heck reaction as disclosed in ref. R. F. Heck, Org. React, 1982, 27, 345). The brown suspension was heated during 24 hours at 110° C. The yellow suspension was filtered at room temperature under silanized silica. The solvent was pumped off under vacuum and a yellow powder was obtained in quantitative yield (2.97 g, 6.7 mmol).

$^1$H NMR (CDCl$_3$, δ, ppm) 7.69 (2H, d), 7.58 (2H, d), 7.20 (2H, s), 3.65 (18H, s). $^{13}$C NMR (CDCl$_3$, δ, ppm) 55.1, 111.9, 114.0, 125.2, 129.6, 139.7. $^{29}$Si NMR (CDCl$_3$, δ, ppm). −55.4. Anal. Calc.; for $C_{20}H_{28}O_6Si_2$: C, 57.12; H, 6.71%. Found; C, 57.86; H, 6.48%.

EXAMPLE 3

Preparation of 4,4'-Bis-(trihydroxysilyl)stilbene)

The procedure of Example 1 was repeated employing 4,4'-bis(trimethoxysilyl)stilbene) in place of bis(trimethoxysilyl)biphenyl (2 g, 4.75 mmol) and using a 1% acetic acid solution (9 ml) to give a ratio of 2.94 equivalents of stilbene to 1 equivalent of acetic acid. The reaction mixture was stirred for a period of 10 days and a yellow coloured powder was recovered at 70% yield. (1.12 g, 3.32 mmol)

$^1$H NMR (DMSO-d6, δ, ppm) 7.69 (4H, d); 7.63 (4H, d); 7.28 (2H, s); 6.41 (6H, s). $^{13}$C NMR (DMSO-d6, δ, ppm)

138.1, 137.5, 135.1, 129.3, 126.0. $^{29}$Si NMR (DMSO-d6, δ, ppm) −54.3. Anal. Calc.; for $C_{14}H_{16}O_6Si_2$: C, 49.98; H, 4.80; Si, 16.70%. Found; C, 50.46; H, 4.95; Si, 16.90%.

EXAMPLE 4

Preparation of 4,4'-Bis(trimethoxysilyl) diphenylacetylene [1-(4-Trimethoxysilyl)phenyl)-2-trimethylsilyl]acetylene A solution of [1-(4-bromophenyl)-2-trimethylsilyl] acetylene (17 g, 0.067 mol) in dry THF (60 ml) was added dropwise to a suspension of chlorotrimethoxysilane (16 g, 0.1 mol) and magnesium chips (2.45 g, 0.1 mol) in dry THF (60 ml) at 10° C. The mixture was then stirred at room temperature for one day. After evaporation of the solvent, the brown mixture was extracted with 200 ml of dry pentane and filtered. The solvent was then pumped off and the brown oil was distilled under vacuum (B.p 78–81° C./10$^{-1}$ mbar) to afford a colourless oil in 46% yield (9 g, 0.031 mol).

$^1$H NMR (CDCl$_3$, δ, ppm) 7.60 (2H, d); 7.47 (2H, d); 3.65 (9H, s); 0.28 (9H, s). $^{13}$C NMR (CDCl$_3$, δ, ppm) 134.9, 131.7, 130.8, 125.7, 105.3, 96.0, 51.2; 0.3. $^{29}$Si NMR (CDCl$_3$, δ, ppm) −17.32, −54.8. Anal. Calc.; for $C_{14}H_{22}O_3Si_2$: C, 57.08; H, 7.52%. Found; C, 57.07; H, 7.52%.

4-(Trimethoxysilyl)phenylacetylene

A solution of [1-(4-trimethoxysilyl)phenyl)-2-trimethylsilyl]acetylene (19.80 g, 0.067 mol) in 41.8 ml of dry methanol was stirred for 4 hours with potassium carbonate (0.84 g, 6.07 mmol) at room temperature. The white suspension was concentrated under vacuum and the residue was extracted with 50 ml of dry pentane. After filtration, the solvent was removed under vacuum to give a crystalline beige powder. This crude solid was crystallised in dry hexane and afforded white crystals of 4-(trimethoxysilyl) phenylacetylene in 72% yield (10.76 g, 0.048 mol). M.p.= 38–39° C.

$^1$H NMR (CDCl$_3$, δ, ppm) 7.62 (2H, d); 7.53 (2H, d); 3.65 (9H, s); 3.17 (1H, s). $^{13}$C NMR (CDCl$_3$, δ, ppm) 135.0, 131.9, 130.8, 124.7, 83.8, 78.8; 51.3. $^{29}$Si NMR (CDCl$_3$, δ, ppm) −55.03. Anal. Calc.; for $C_{11}H_{14}O_3Si$: C, 59.44; H, 6.34, Si, 12.64%. Found; C, 59.85; H, 6.30, Si, 13.30%.

4,4'-Bis-(trimethoxysilyl)diphenylacetylene

A solution of 4-(trimethoxysilyl)phenylacetylene (1.03 g, 4.62 mmol) in dry triethylamine (13.5 ml) with a stoichiometric amount of 4-iodo(1-trimethoxysilyl)benzene (1.5 g, 4.62 mmol) was stirred for a few minutes. 3% molar of CuI (26 mg, 0.138 mmol) and bis-(triphenylphosphine) palladium chloride II (100 mg, 0.138 mmol) were added all at once, the final brown suspension was stirred vigorously for 8 hours at ~20° C. The brown suspension was concentrated under vacuum and the dark residue was extracted with 50 ml of dry toluene.

The yellow suspension was filtered on silanized silica and concentrated under vacuum. The expected product was obtained as a fine yellow powder (1.88 g, 4.49 mmol) in 97% yield.

$^1$H NMR (CDCl$_3$, δ, ppm) 7.68 (4H, m); 7.59 (4H, d); 3.67 (18H, s). $^{13}$C NMR (CDCl$_3$, δ, ppm) 135.1, 131.4, 130.2, 125.7, 90.9, 51.3. $^{29}$Si NMR (CDCl$_3$, δ, ppm) −54.8. Anal. Calc.; for $C_{20}H_{26}O_6Si_2$: C, 57.39; H, 6.16; Si, 13.42%. Found; C, 57.23; H, 5.85; Si, 13.45%.

EXAMPLE 5

4,4'-Bis-(trimethoxysilyl)diphenylbut-1,3-diyne 2 g (9 mmol) of 4-(trimethoxysilyl)phenylacetylene, one equivalent of chloroacetone (0.67 g, 9 mmol), two equivalents of dry triethylamine (2.51 ml), 7.6% molar of CuI (130 mg, 0.68 mmol) and 3% molar of tetrakis-(triphenylphosphine)palladium (312 mg, 27 mmol) were added all at once. The final black solution was stirred for 24 hours at 20° C.

The resulting black suspension was concentrated under vacuum and the dark residue was extracted with 50 ml of dry pentane. The residual dark suspension was filtered on silanized silica and concentrated under vacuum. The black crude oil was crystallised twice in dry pentane and afforded the expected product as a yellow fine powder in 67% yield (1.58 g, 3.31 mmol) (M.p 57–59° C.). $^1$H NMR (CDCl$_3$, δ, ppm) 7.66 (4H, d); 7.56 (4H, d); 3.66 (18H, s). $^{13}$C NMR (CDCl$_3$, δ, ppm) 135.1, 132.2, 131.5, 124.2, 82.2, 75.3, 51.3. $^{29}$Si NMR (CDCl$_3$, δ, ppm) −55.3. Anal. Calc.; for $C_{25}H_{26}O_6Si_2$: C, 62.74; H, 5.40; Si, 11.73%. Found; C, 60.05; H, 5.56; Si, 13.20%.

EXAMPLE 6

1,4-Bis-[2-(4-trimethoxysilylphenyl)ethynyl] benzene

A solution of 4-(trimethoxysilyl)phenylacetylene (1 g, 4.50 mmol) in dry triethylamine (12.5 ml) with a 0.5 eq. of 1,4-diodobenzene (0.74 g, 2.25 mmol) was stirred for few minutes.

5% molar of CuI (21 mg, 0.112 mmol) and bis-(triphenylphosphine)palladium chloride II (80 mg, 0.112 mmol) were added all at once, the final brown suspension was stirred vigorously for 8 hours at ~20° C. The brown suspension was concentrated under vacuum and the dark residue was extracted with 50 ml of dry toluene. The yellow suspension was filtered on silanized silica and concentrated under vacuum. The expected product was obtained as a fine yellow-orange powder. Crystallisation in hexane/dichloromethane gave the expected product as an orange powder (1.88 g, 4.49 mmol) in 97% yield. M.p.=164–166° C. $^1$H NMR (CDCl$_3$, δ, ppm) 7.69 (4H, d), 7.59 (4H, d), 7.55 (4H, s), 3.67 (18 H, s). $^{13}$C NMR (CDCl$_3$, δ, ppm) 135.1, 132.0, 131.4, 130.4, 125.6, 123.5, 91.6, 90.8, 51.3. $^{29}$Si NMR (CDCl$_3$, δ, ppm). −55.9. Anal. Calc.; for $C_{28}H_{30}O_6Si_2$: C, 64.48; H, 5.78; Si, 10.83%. Found; C, 63.42; H, 5.73; Si, 11.75%.

EXAMPLE 7

4,4'-Bis-(trihydroxysilyl)diphenylacetylene

A solution of 4,4'-bis-(trimethoxysilyl)diphenylacetylene (1.58 g, 3.77 mmol) in 10 ml of ether was stirred vigorously with 29 ml of 0.5% acetic acid solution for 41 days. The beige suspension was filtered and the resulting solid was washed three times with acetone and ether. The resulting beige solid was dried for one day under vacuum at room temperature and yield (970 mg, 2.9 mmol) (77%). $^1$H NMR (DMSO-d$_6$, δ, ppm) 7.63 (4H, d); 7.50 (4H, d), 6.52 (6H, s). $^{13}$C NMR (DMSO-d$_6$, δ, ppm) 139.3, 135.2, 130.9, 123.6, 90.7. $^{29}$Si NMR (DMSO-d$_6$, δ, ppm) −55.2. IRFT (KCl, cm$^{-1}$) ν(Si—OH), 3195; ν(C≡C$_{Ar}$), 1601; ν(Si—C$_{Ar}$), 1128. Anal. Calcd.; For $C_{14}H_{14}O_6Si_2$: C, 50.24; H, 4.22% Si, 16.70. Found: C, 48.99; H, 3.96; Si, 15.00%.

EXAMPLE 8

4,4'-Bis-(trihydroxysilyl)diphenylbut-1,3-diyne

A solution of 4,4'-bis-(trimethoxysilyl)diphenylbut-1,3-diyne (1.15 g, 2.40 mmol) in 10 ml of ether was stirred vigorously with 13.70 ml of 0.5% acetic acid solution for 36 days. The beige suspension was filtered and the solid was washed three times with ethanol, acetone and ether. The resulting beige crystalline solid was dried for one day under vacuum at room temperature and the expected product was obtained in 65% yield (750 mg, 1.56 mmol).

$^1$H NMR (DMSO-d$_6$, δ, ppm) 7.65 (4H, d); 7.57 (4H, d); 6.58 (6H, s). $^{13}$C NMR (DMSO-d$_6$, δ, ppm) 140.9, 135.2, 131.9, 121.6, 83.1, 74.7. $^{29}$Si NMR (DMSO-d$_6$, δ, ppm) −55.6. IRFT (KCl, cm$^{-1}$) ν(Si—OH), 3208; ν(C═C$_{Ar}$), 1594; ν(Si—C$_{Ar}$), 1126. Anal. Calcd.; For C$_{16}$H$_{14}$O$_6$Si$_2$: C, 53.62; H, 3.93; Si, 15.67%. Found: C, 53.04; H, 3.75; Si, 16.35%.

EXAMPLE 9

1,1'-Bis-(trihydroxysilyl)ferrocene

A solution of 1,1' bis-(trimethoxysilyl)ferrocene (1.25 g, 2.93 mmol) in 3 ml of ether was stirred vigorously with 1.37 ml of 0.5% acetic acid solution for 75 days. The final orange suspension was filtered and the solid was washed three times with ethanol, acetone and ether.

The resulting orange crystalline solid was dried for one day under vacuum at room temperature and the expected product was obtained in 69% yield (0.59 g, 2 mmol).

$^1$H NMR (DMSO-d$_6$, δ, ppm) 4.3 (4H); 4.2 (4H); 6.46 (6H, s). $^{13}$C NMR (DMSO-d$_6$, δ, ppm) 74.8, 71.3, 68.6. $^{29}$Si NMR (DMSO-d$_6$, δ, ppm) −54.2.

EXAMPLE 10

Chloromethyldiisopropyloxysilane

A solution of trichloromethylsilane (29.9 g, 200 mmol) in 200 ml of anhydrous pentane was placed in a schlenck tube under an argon atmosphere at 0° C. A solution of 2.2 equivalents of dry ispropanol (26.4 g, 440 mmol) was then added dropwise. The evolution of HCl was trapped by a concentrated solution of NaOH. At the end of addition the reaction mixture was allowed to warm to room temperature and then stirred during 24 hours. After this time the colourless solution was evaporated under vacuum (2 mBar) to give a colourless oil (36 g). It consisted in a mixture of chloromethyldiisopropyloxysilane (~80%) and methyltriisopropyloxysilane (~20%). $^1$H NMR (CDCl$_3$, δ, ppm): 4.37 (2H, sept), 1.26 (12H, d), 0.48 (3H, s).

4-Bromo-1-(methyldiisopropyloxysilyl)benzene

A solution of 4-bromophenyl magnesium bromide (7.82 g, 50 mmol) in THF (100 ml) was added at 0° C. to a solution of chloromethyldiisopropyloxysilane (10 g, 48 mmol). The mixture was stirred at room temperature for 24 hours. After evaporation of the solvent, the yellow solid was extracted by 200 ml of dry pentane and filtered. The solvent was then pumped off to afford a yellow oil. Residual 1,4-dibromobenzene was sublimated under vacuum at 80° C. to give 4-bromo-1-(methyldiisopropyloxysilyl)benzene as a colourless oil in 33% yield (5.1 g, 16 mmol). $^1$H NMR (CDCl$_3$, δ, ppm) 7.52 (4H, m); 4.22 (2H, heptuplet); 1.24 (12H, d); 0.39 (3H, s). $^{13}$C NMR (CDCl$_3$, δ, ppm) 136.1, 134.5, 131.3, 125.1, 65.8, 26.1, −2.8. $^{29}$Si NMR (CDCl$_3$, δ, ppm) −21.8.

4-Iodo-1-(methyldiisopropyloxysilyl)benzene

A solution of 4-bromo-1-(methyldiisopropyloxysilyl) benzene (13.35 g, 42.1 mmol) in THF (85 ml) was added slowly dropwise at 0° C. to a suspension of magnesium chips (1.53 g, 63.1 mmol) in THF (10 ml). After one hour, the Grignard reagent of 4-bromo-1-(methyldiisopropyloxysilyl)benzene was added dropwise at 0° C. to iodine (13.87 g, 54 mmol) dissolved in 50 ml of dry THF. After stirring during four hours, the solvent was pumped off and the residue was extracted with dry pentane (200 ml) and filtered. The yellow solution was concentrated to afford 4-iodo-1-(methyldiisopropyloxysilyl)benzene as a yellow oil of in 84% yield. $^1$H NMR (CDCl$_3$, δ, ppm) 7.76 (2H, d); 7.42 (2H, d); 4.21 (2H, heptuplet); 1.23 (12H, t); 0.37 (3H, s).

4-Iodo-1-(methyldimethoxysilyl)benzene

Compound 4-iodo-1-(methyldiisopropyloxysilyl)benzene (11.27 g, 35.5 mmol) was dissolved in dry methanol (12.87 g, 400 mmol). 1% molar of p-toluene sulfonic acid (53 mg, 0.3 mmol) was added all at once. The yellow suspension was stirred for 4 hours. The organic solvent was pumped off and the corresponding crude orange oil was distilled under vacuum (B.p. 59–69° C., 3.10$^{-1}$ mbar) to afford 4-iodo-1-(methyldimethoxysilyl)benzene as a colourless oil (9 g, 30 mmol) in 82% yield. $^1$H NMR (CDCl$_3$, δ, ppm) 7.78 (2H, d); 7.37 (2H, d); 3.58 (6H, s); 0.37 (3H, s).

[1-(4-(Methyldimethoxysilyl)phenyl), 2-Trimethylsilyl]acetylene

A solution of 4-iodo-1-(methyldimethoxysilyl)benzene (5.38 g, 17.4 mmol) dissolved in dry triethylamine (50 ml) with a stoichiometric amount of trimethylsilylacetylene (1.76 g, 17.4 mmol) was added all at once to give a colourless solution. 2.5% molar of CuI (85 mg, 0.44 mmol) and bis-(triphenylphosphine)palladium chloride II (320 mg, 0.44 mmol) were added and the final brown suspension was stirred vigorously for 2 hours at ~20° C. The brown suspension was concentrated under vacuum and the residue was extracted with 150 ml of dry pentane. The suspension was filtered on silanized silica and concentrated under vacuum. The expected product [1-(4-(methyldimethoxysilyl)phenyl), 2-trimethylsilyl]acetylene was obtained as a greenish oil (1.88 g, 4.49 mmol) in quantitative yield. $^1$H NMR (CDCl$_3$, δ, ppm) 7.59 (2H, d); 7.49 (2H, d); 3.58 (6H, s); 0.39 (3H, s); 0.29 (9H, s).

4-(Methyldimethoxysilyl)phenylacetylene

A solution of [1-(4-(methyldimethoxysilyl)phenyl), 2-trimethylsilyl]acetylene (5 g, 17.80 mmol) in 11 ml of dry methanol was stirred for 3.5 hours with potassium carbonate (224 mg, 1.62 mmol) at room temperature. The dark suspension was concentrated under vacuum and the residue was extracted with 60 ml of dry hexane. After filtration, the solvent was removed under vacuum to give 4-(methyldimethoxysilyl)phenylacetylene as a red oil (2.8 g, 13.5 mmol) in 75% yield. $^1$H NMR (CDCl$_3$, δ, ppm) 7.59 (2H, d); 7.55 (2H, d); 3.59 (6H, s); 3.16 (1 H, s); 0.39 (3H, s)

4,4'Bis-(methyldimethoxysilyl)diphenylacetylene

A solution of [1-(4-(methyldimethoxysilyl)phenyl), 2-trimethylsilyl]acetylene (0.96 g, 4.64 mmol) in dry triethylamine (15 ml) with a stoichiometric amount of 4-iodo-1-(methyldimethoxysilyl)benzene (1.43 g, 4.64 mmol) was stirred during few minutes. 2.5% molar of CuI (23 mg, 0.12 mmol) and bis-(triphenylphosphine)palladium chloride II (82 mg, 0.12 mmol) were added all at once, the final beige suspension was stirred vigorously for 15 hours at ~20° C. The corresponding suspension was filtered on silanized silica and concentrated under vacuum. The expected product 4,4'-bis-(methyldimethoxysilyl)diphenylacetylene was obtained as an orange oil (1.72 g, 4.44 mmol) in 96% yield. $^1$H NMR (CDCl$_3$, δ, ppm) 7.65 (4H, m); 7.57 (4H, d); 3.60 (12H, s); 0.40 (6H, s). $^{13}$C NMR (CDCl$_3$, δ, ppm) 134.69, 134.32, 131.35, 112.24, 90.73, 50.98, −4.79. $^{29}$Si NMR (CDCl$_3$, δ, ppm) −14.46.

EXAMPLE 11

4,4'-Bis-(methyldimethoxysilyl)diphenylbut-1,3-diyne

In a schlenk tube under argon, 1.66 g (8.04 mmol) of 4-(methyldimethoxysilyl)phenylacetylene, one equivalent of chloroacetone (0.745 g, 8.04 mmol), two equivalents of dry ethylamine (2.3 ml), 7.6% molar of CuI (116 mg, 0.61 mmol) and tetrakis-(triphenylphosphine) palladium 0 (280 mg, 0.61 mmol) were added all at once. The final black solution was stirred for 4.5 hours at ~20° C. The residual dark suspension was filtered on silanized silica and concentrated under vacuum to afford a crude yellow oil. It was crystallised two times in dry pentane and afforded 4,4'bis-(methyldimethoxysilyl)diphenylbut-1,3-diyne as a yellow fine powder (1 g, 2.43 mmol) (M.p. 85–86° C.) in 61% yield. $^1$H NMR (CDCl$_3$, δ, ppm) 7.64 (4H, d); 7.57 (4H, d); 3.60 (12H, s); 0.39 (6H, s). $^{29}$Si NMR (CDCl$_3$, δ, ppm) −14.80.

EXAMPLE 12

4,4'-Bis-(methyldihydroxysilyl)diphenylacetylene

A suspension of 4,4'-bis-(methyldimethoxysilyl) diphenylacetylene (1.62 g, 4.2 mmol) in 8 ml of ether was stirred vigorously with 6.65 ml of 0.5% acetic acid solution for 55 days. The beige suspension was filtered and the solid was washed three times with acetone and ether. The resulting fine beige solid was dried for one day under vacuum at room temperature and gave 4,4'-bis-(methyldihydroxysilyl) diphenylacetylene in 30% yield (410 mg, 1.26 mmol). $^1$H NMR (DMSO-d$_6$, δ, ppm) 7.63 (4H, s); 7.54 (4H, s); 6.49 (4H, s); 0.19 (6H, s). $^{13}$C NMR (DMSO-d$_6$, δ, ppm) 141.2, 134.5, 131.2, 123.7, 90.8, 0.18. $^{29}$Si NMR (DMSO-d$_6$, δ, ppm) −21.7.

EXAMPLE 13

1,4-Bis-(dimethoxymethylsilyl)benzene

A solution of 1,4-dibromobenzene (24.75 g, 105 mmol) in 60 ml of anhydrous THF, was added dropwise to a suspension of magnesium (12.60 g, 518 mmol) and methyltrimethoxysilane (28.60 g, 210 mmol) in 20 ml of anhydrous THF at 0° C. The suspension was then stirred 24 hours at 20° C. The solvent was pumped off under vacuum (2 mBar), the reaction mixture was then taken up with 250 ml of dry pentane. The green suspension was filtered. The filtrate was evaporated under vacuum (2 mBar) to give a pale yellow oil which was distilled. (B.p. 105–110° C./5 10$^{-1}$ mBar) (7.38 g, 26.5 mmol) of 1,4-bis-(dimethoxymethylsilyl)benzene were obtained as a colourless oil which crystallised at room temperature in 25% yield. $^1$H NMR (CDCl$_3$, δ, ppm): 7.67 (4H, s), 3.60 (12H, s), 0.39 (6H, s). $^{29}$Si NMR (CDCl$_3$, δ, ppm): −14.90. Anal. Calc. For C$_{12}$H$_{22}$O$_4$Si$_2$: C, 50.35; H, 7.69; Si, 19.58%. Found: C, 50.30; H, 7.64; Si, 20.01%.

EXAMPLE 14

1,4-Bis-(dimethoxymethylsilyl)biphenyl

A solution of 4,4'-dibromobiphenyl (25 g, 80 mmol) in 120 ml of anhydrous THF, was added dropwise to a suspension of magnesium (7.80 g, 321 mmol) and methyltrimethoxysilane (30 g, 220 mmol) in 50 ml of anhydrous THF at 0° C. The pale green suspension was then stirred 24 hours at 20° C. The solvent was pumped off under vacuum (2 mBar), the reaction mixture was then taken up with 200 ml of dry pentane. The grew suspension was filtered. The filtrate was evaporated under vacuum (2 mBar) to give a pale yellow oil which was distilled. (B.p. 63–171° C./5 10$^{-1}$ mBar) (2.8 g, 28 mmol) of 1,4-bis-(dimethoxymethylsilyl) biphenyl were obtained as a colourless oil in 10% yield. $^1$H NMR (CDCl$_3$, δ, ppm): 7.72 (4H, d), 7.67 (4H, d), 3.65 (12H, s), 0.44 (6H, s). $^{29}$Si NMR (CDCl$_3$, δ, ppm): −14.7.

EXAMPLE 15

4,4'-Bis-(methyldihydroxysilyl)benzene

A suspension of 4,4'-bis-(methyldimethoxysilyl)benzene (1 g, 3.49 mmol) in 5 ml of ether was stirred vigorously with 1.6 ml of 0.5% acetic acid solution for two hours. The white suspension was filtered and the solid was washed three times with acetone and ether.

The resulting fine white solid was dried for one day under vacuum at room temperature and gave 4,4'-bis-(methyldihydroxysilyl)benzene in 95% yield (0.76 g, 3.31 mmol). $^1$H NMR (DMSO-d$_6$, δ, ppm) 7.53 (4H, s); 6.32 (4H, s); 0.14 (6H, s). $^{13}$C NMR (DMSO-d$_6$, δ, ppm) 141, 133.2, 0.35. $^{29}$Si NMR (DMSO-d$_6$, δ, ppm) −21.28. Anal. Calcd.; For C$_8$H$_{14}$O$_4$Si$_2$: C, 41.71; H, 6.12; Si, 25.38%. Found: C, 41.51; H, 6.19; Si, 25.30%.

EXAMPLE 16

4,4'-Bis-(methyldihydroxysilyl)biphenyl

A suspension of 4,4'-bis-(methyldimethoxysilyl)biphenyl (2.4 g, 6.62 mmol) in 5 ml of ether was stirred vigorously with 3 ml of 0.5% acetic acid solution for 32 days. The white suspension was filtered and the solid was washed three times with acetone and ether. The resulting fine white solid was dried for one day under vacuum at room temperature and gave 4,4'bis-(methyldihydroxysilyl)biphenyl in 32% yield (0.65 g, 2.10 mmol). $^1$H NMR (DMSO-d$_6$, δ, ppm) 7.66 (8H, s); 6.40 (4H, s); 0.19 (6H, s). $^{13}$C NMR (DMSO-d$_6$, δ, ppm) 144.7, 139.3, 134.9, 126.6, 0.38. $^{29}$Si NMR (DMSO-d$_6$, δ, ppm) −21.22. Anal. Calcd.; For C$_{14}$H$_{18}$O$_4$Si$_2$: C, 54.87; H, 5.92; Si, 18.33%. Found: C, 54.82; H, 5.79; Si, 18.80%.

EXAMPLE 17

4-(Methyldiisopropyloxysilyl)styrene

A solution of 4-chlorostyrene (10 g, 72 mmol) in 40 ml of anhydrous THF, was added dropwise to a suspension of magnesium chips (2.07 g, 86.4 mmol) and chloromethyldiisopropyloxysilane (28.2 g, 144 mmol) in 50 ml of anhydrous THF at 0° C. The suspension was then stirred 24 hours at 20° C. The solvent was pumped off under vacuum (2 mBar), the reaction mixture was then taken up with 200 ml of dry pentane. The suspension was filtered. The filtrate was evaporated under vacuum (2 mBar) to give an oil which was distilled. (Eb. 70–75° C./5 10$^{-2}$ mBar) (8.23 g, 31 mmol) of 4-(methyldiiosoprppyloxysilyl)styrene were obtained as a colourless oil in 51% yield. $^1$H NMR (CDCl$_3$, δ, ppm): 7.65 (2H, d), 7.44 (2H, d), 6.75 (1H, dd), 5.80 (1H, d), 5.30 (1H, d), 4.22 (1H, heptuplet), 1.22 (12H, d), 0.39 (3H, s).

4-(Methyldimethoxysilyl)styrene

Compound 4-(methyldiisopropyloxysilyl)styrene (8.23 g, 31 mmol) was dissolved in dry methanol (10 ml,). 1% molar of p-toluene sulfonic acid (17 mg) was added all at once. The yellow suspension was stirred for 4 hours. The organic solvent was pumped off and the corresponding crude oil was distilled under vacuum (B.p. 70–80° C., $5.10^{-2}$ mbar) to afford 4-(methyldimethoxysilyl)styrene as a yellow oil (4 g, 20 mmol) in 65% yield. $^1$H NMR (CDCl$_3$, δ, ppm) 7.64 (2H, d); 7.49 (2H, d); 6.77 (1H, dd), 5.84 (1H, d), 5.33 (1H, d), 3.60 (6H, s); 0.39 (3H, s).

4-Bromol-(methyldimethoxysilyl)benzene

Compound 4-bromol-(methyldiisopropyloxysilyl) benzene (5 g, 16 mmol) was dissolved in dry methanol (20 ml). 1% molar of p-toluene sulfonic acid (30 mg,) was added all at once. The suspension was stirred for 4 hours. The organic solvent was pumped off and the corresponding crude oil was 4-bromol-(methyldimethoxysilyl)benzene (2 g, 8 mmol) in 50% yield. $^1$H NMR (CDCl$_3$, δ, ppm) 7.56 (4H, m); 3.59 (6H, s); 0.38 (3H, s)

4,4'-Bis(methyldimethoxysilyl)stilbene

A solution of 4-(methyldimethoxysilyl)styrene (1.52 g, 7.2 mmol) and 4-bromol-(methyldiisopropyloxysilyl) benzene (1.9 g, 7.2 mmol) was dissolved in 15 ml toluene. Palladium acetate (81 mg, 3.6 $10^{-4}$ mol), dry triethylamine (4.39 g, 43.2 mmol) and tri-orthotolylphosphine (TOP) (438 mg, 1.5 $10^{-3}$ mol) were added all at once successively. The suspension was heated during 24 hours at 120° C. The resulting suspension was filtered at room temperature over silanized silica. The solvent was pumped off under vacuum and a yellow powder was recovered. It was recrystallized in pentane. 4,4'-bis(methyldimethoxysilyl)stilbene (1.54 g, 3.96 mmol) was obtained (yield 55%). $^1$H NMR (CDCl$_3$, δ, ppm) 7.65 (4H, d); 7.61 (4H, d), 7.19 (2H, s), 3.60 (12H, s); 0.39 (3H, s).

EXAMPLE 18

4,4'-bis(methyldihydroxysilyl)stilbene was prepared from 4,4'bis-(methyldimethoxysilyl)stilbene by the procedure of Example 16. 4,4'bis-(methyldihydroxysilyl)stilbene had $^1$H NMR (DMSO-d$_6$, δ, ppm) 7.68 (4H, d); 7.59 (4H, d), 7.29 (2H, s), 6.37 (4H, s); 0.39 (6H, s). $^{13}$C NMR (DMSO-d$_6$, δ, ppm) 139.7, 138.1, 134.7, 129.5, 126.4, 0.02. $^{29}$Si NMR (DMSO-d$_6$, δ, ppm) −21.36.

EXAMPLES 19 to 22

Resin Compositions 90 wt. % of the base resin [(PhSiO$_{3/2}$)$_{0.40}$(MeSiO$_{3/2}$)$_{0.45}$(PhMeSiO)$_{0.1}$(Ph$_2$SiO)$_{0.05}$] was mixed with 10 wt. % of a compound (B) as a solution in an appropriate solvent as listed below, together with 0.2 wt. % of a mixture of zinc dioctoate and choline octoate) as the curing catalyst.

Example 19—1,4-bis(dimethoxymethylsilyl)benzene prepared in Example 13; solvent tetrahydrofuran (THF)

Example 20—4,4'-bis(trimethoxysilyl)biphenyl prepared as described by Corriu et al., Chem. Mater., (1992), 4, 1217–1224; solvent toluene.

Example 21—4,4'-bis(trihydroxysilyl)diphenylbut-1,3-diyne prepared in Example 8; solvent dimethylsulphoxide (DMSO)

Example 22—1,4-bis(trihydroxysilyl)benzene; solvent DMSO

After mixing the majority of the solvent was removed at 80° C. under vacuum and the resin blend was cured through a fourteen day curing cycle. During cure, the temperature was gradually raised from 80° C. to 260° C. to obtain a cured cast plate. Specimens for dynamic mechanical analysis (DMA) were obtained by cutting 1×6×25 mm pieces from the casting. DMA was done from −155° C. to 500° C. at 1 Hz in a tensile mode; the oscillation amplitude was 5 microns. The storage modulus and loss factor tan δ were recorded. or flexural testing, the three point bending test was performed on an Instron 8562 (Trade Mark) test machine per ASTM standard D 790. The plane strain fracture toughness, $K_{Ic}$, was obtained per ASTM D 5045, and the critical strain energy release rate, $G_{Ic}$, (fracture energy) was calculated from $K_{Ic}$ based on Linear Elastic Fracture Mechanics assumptions.

A base resin casting without addition of compound (B) was also cured and analysed in the same way as a comparison.

The results for Examples 19 and 20 are shown in Table 1 below

TABLE 1

|  | Example 19 | Cured base resin | Example 20 |
| --- | --- | --- | --- |
| Young's Modulus (GPa) | 1.82 | 1.88 | 1.73 |
| Strain at break % | 2.80 | 2.46 | 2.54 |
| Flexural strength (MPa) | 37.8 | 37.7 | 33.9 |
| Fracture toughness $K_{Ic}$ (MPam$^{1/2}$) | 0.260 | 0.253 | 0.308 |
| Fracture Energy (J/m$^2$) | 42.5 | 38.3 | 54.8 |

It can be seen that the incorporation of each compound (B) into the resin structure slightly lowers the resin's Young's modulus, but increases the fracture toughness ($K_{Ic}$) and the critical energy release rate $G_{Ic}$. The fracture toughness $K_{Ic}$ measures the difficulty of initiating a crack in the material, while the $G_{Ic}$ measures how much energy per unit area it needs to propagate a crack in the material once the crack is initiated. The modified resin of Example 19 is slightly tougher than the unmodified resin, and the modified resin of Example 20 is substantially tougher than the unmodified resin.

Figure 1:
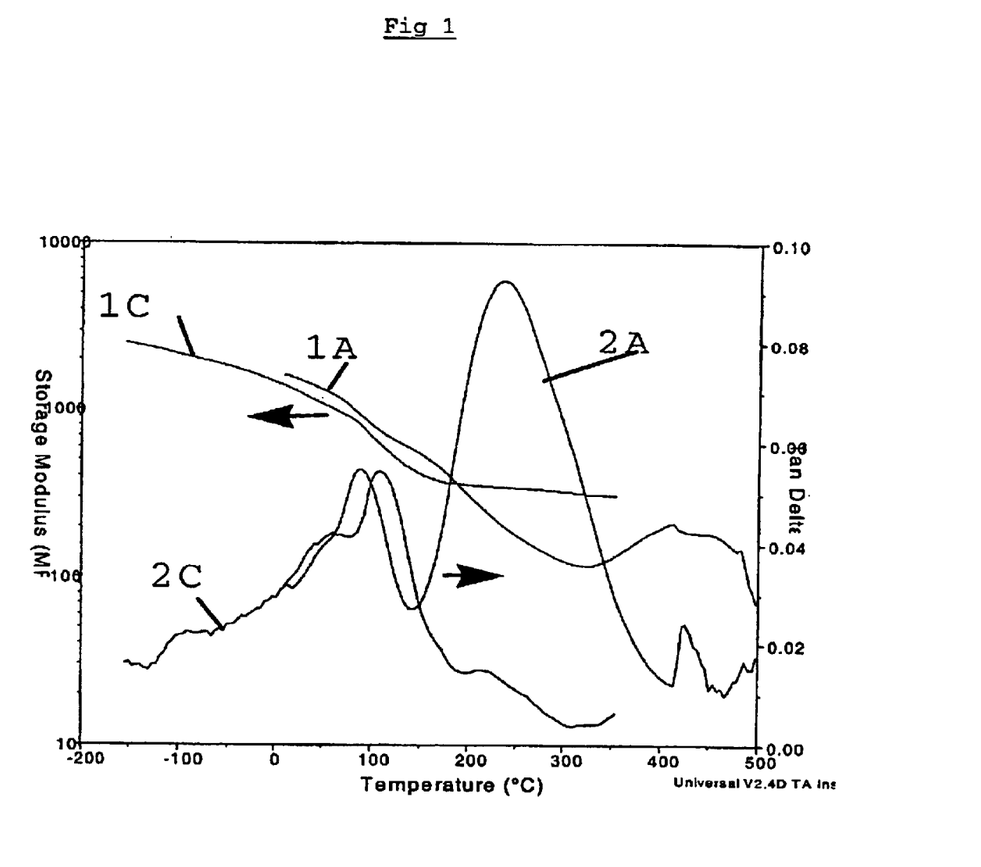
FIG. 1 is a graph showing the dynamic mechanical analysis results of Example 21.

For Example 21, the storage modulus (1A) and loss factor(tan δ, (2A)) of the modified resin are plotted in FIG. 1, together with the storage modulus (1C) and loss factor (2C) of the unmodified resin. The high temperature transition peak of the tan δ curve was much enhanced by the incorporation of the 4,4'-bis(trihydroxysilyl)diphenylbut-1,3-diyne. The addition of this modifier significantly enhances the mechanical damping capability of the resin in the temperature range 150–350° C. This damping capability is important for applications where mechanical vibration needs to be mitigated.

Figure 2:
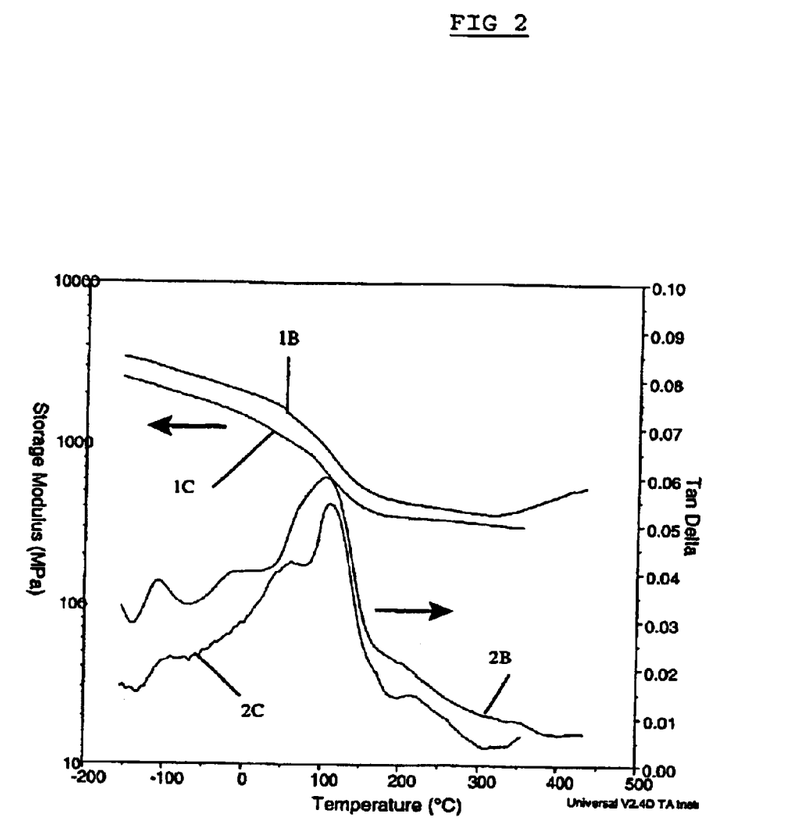
FIG. 2 is a graph showing the dynamic mechanical analysis results of Example 22.

For Example 22, the storage modulus (1B) and loss factor (2B) of the modified resin are plotted in FIG. 2, together with the storage modulus (1C) and loss factor (2C) of the unmodified resin. With 10 wt. % 1,4-bis(trihydroxysilyl) benzene reacted into the resin, the storage modulus is much higher, approximately twice that of the unmodified resin throughout the whole temperature range, even though the modulus dependence on temperature was quite similar and no obvious shift of glass transition temperature was seen. Both had a glass transition temperature at about 100° C. The much higher modulus above the glass transition temperature indicated a higher crosslink density in the modified resin.

What is claimed is:

1. A curable silicone resin composition comprising (A) an uncured silicone resin having units of the formula $(R^*)_a(R)_b$ $SiO_{(4-a-b)/2}$, where each R* is a functional group capable of reacting with Si—OH and/or Si-alkoxy groups and each R is a nonfunctional monovalent hydrocarbon group, a+b is from 1.0 to 3.0 and each molecule of uncured silicone resin contains an average of at least two groups R*, and (B) a silanol or hydrolysable compound of the formula where each R' represents a hydroxyl group or a hydrolysable group; each R" represents hydrogen, a monovalent hydrocarbon which optionally is substituted, or a group within the above definition of R'; and Ar is a substantially nonflexible linkage including at least one para-arylene moiety, so that the groups $(R')_hR"Si—$ are spatially separated
wherein (A) and (B) are present in amounts to have a weight ratio of (A) to (B) of 5:1 to 20:1.

2. A composition according to claim 1, wherein Ar is a 1,4-phenylene linkage which is optionally substituted by one or more alkyl, aryl, aralkyl or alkenyl group or may be part of a fused ring system.

3. A composition according to claim 1, wherein Ar comprises two to four 1,4-phenylene moieties, each optionally substituted by one or more alkyl, aryl, aralkyl or alkenyl group, linked in a substantially linear conformation.

4. A composition according to claim 3, wherein the 1,4-phenylene moieties are linked by a direct bond or by an acetylene or butadiyne linkage or by an optionally substituted vinylene linkage.

5. A composition according to claim 1, wherein R' is a hydroxyl group or an alkoxy group having 1 to 6 carbon atoms.

6. A composition according to claim 1, wherein R" is an alkyl group having 1 to 6 carbon atoms or a phenyl group.

7. A composition according to claim 1, wherein the uncured silicone resin has the empirical formula $(R^*)_a(R)_b SiO_{(4-a-b)/2}$ where a+b is between 0.8 and 1.6.

8. An organobis(silanetriol) of the formula $(HO)_3Si—Ar'—Si(OH)_3$ wherein Ar' is a linkage containing two or more phenylene moieties held in a substantially linear conformation so that the silanetriol groups are spatially separated.

9. An organobis(silanetriol) according to claim 8, wherein Ar' comprises two to four 1,4-phenylene groups linked by a direct bond or by an acetylene or butadiyne linkage or by a vinylene linkage, each 1,4-phenylene group being optionally substituted by one or more alkyl, aryl, aralkyl or alkenyl group or being optionally part of a fused ring system.

10. An organosilicon compound of the formula wherein each R' represents a hydroxyl group or a hydrolysable group and each R" represents hydrogen, a monovalent hydrocarbon which optionally is substituted, or a group within the above definition of R', each Ap is a para-arylene moiety, and X is a substantially inflexible linkage having at least two carbon atoms so that the groups $(R')_2R"Si—$ are spatially separated.

11. An organosilicon compound according to claim 10, wherein X comprises at least one acetylene, butadiyne or vinylene linkage, or a para-arylene moiety.

12. An organosilicon compound according to claim 10, wherein Ap is a 1,4-phenylene linkage that is optionally substituted by one or more alkyl, aryl, aralkyl or alkenyl group or may be part of a fused ring system.

13. A process for forming a cured silicone resin composition, comprising mixing (A) an uncured silicone resin having units of the formula $(R^*)_a(R)_b SiO_{(4-a-b)/2}$, where each R* is a functional group capable of reacting with Si—OH and/or Si-alkoxy groups and each R is a nonfunctional monovalent hydrocarbon group, a+b is from 1.0 to 3.0 and each molecule of uncured silicone resin contains an average of at least two groups R*, with (B) a silanol or hydrolysable compound of the formula where each R' represents a hydroxyl group or a hydrolysable group; each R" represents hydrogen, a monovalent hydrocarbon which optionally is substituted, or a group within the above definition of R'; and Ar is a substantially nonflexible linkage including at least one para-arylene moiety, so that the groups $(R')_2R"Si—$ are spatially separated, and curing the composition under conditions such that (A) and (B) are copolymerised wherein (A) and (B) are present in amounts to have a weight ratio of (A) to (B) of 5:1 to 20:1.

14. A method of toughening a curable silicone resin comprising mixing (A) an uncured silicone resin having units of the formula $(R^*)_a(R)_b SiO_{(4-a-b)/2}$, where each R* is a functional group capable of reacting with Si—OH and/or Si-alkoxy groups and each R is a nonfunctional monovalent hydrocarbon group, a+b is from 1.0 to 3.0 and each molecule of uncured silicone resin contains an average of at least two groups R*, and (B) a silanol or hydrolysable compound of the formula where each R' represents a hydroxyl group or a hydrolysable group; each R" represents hydrogen, a monovalent hydrocarbon which optionally is substituted, or a group within the above definition of R'; and Ar is a substantially nonflexible linkage including at least one para-arylene moiety, so that the groups $(R')_2R"Si—$ are spatially separated wherein (A) and (B) are present in amounts to have a weight ratio of (A) to (B) of 5:1 to 20:1.

15. A method according to claim 14, wherein the uncured silicone resin (A) has the empirical formula $(R^*)_a(R)_b SiO_{(4-a-b)/2}$ where a+b is between 0.8 and 1.6.

16. A method according to claim 14, wherein Ar is a 1,4-phenylene linkage which is optionally substituted by one or more alkyl, aryl, aralkyl or alkenyl group or may be part of a fused ring system.

17. A process for preparing a substrate having a cured silicone resin film thereon, comprising mixing (A) an uncured silicone resin having units of the formula $(R^*)_a(R)_b SiO_{(4-a-b)/2}$, where each R* is a functional group capable of reacting with Si—OH and/or Si-alkoxy groups and each R is a nonfunctional monovalent hydrocarbon group, a+b is from 1.0 to 3.0 and each molecule of uncured silicone resin contains an average of at least two groups R*, and (B) a silanol or hydrolysable compound of the formula where each R' represents a hydroxyl group or a hydrolysable group; each R" represents hydrogen, a monovalent hydrocarbon which optionally is substituted, or a group within the above definition of R'; and Ar is a substantially nonflexible linkage including at least one para-arylene moiety, so that the groups (R')$_2$R"Si— are spatially separated; wherein (A) and (B) are present in amounts to have a weight ratio of (A) to (B) of 5:1 to 20:1; in a solvent; coating the resulting solution on a substrate; drying the coating; and subjecting the coating to curing conditions.

18. A method according to claim 17, wherein the uncured silicone resin (A) has the empirical formula $(R^*)_a(R)_b SiO_{(4-a-b)/2}$ where a+b is between 0.8 and 1.6.

19. A method according to claim 17, wherein Ar is a 1,4-phenylene linkage which is optionally substituted by one or more alkyl, aryl, aralkyl or alkenyl group or may be part of a fused ring system.

20. A process for producing a moulded cured silicone resin, comprising mixing (A) an uncured silicone resin having units of the formula $(R^*)_a(R)_b SiO_{(4-a-b)/2}$, where each R* is a functional group capable of reacting with Si—OH and/or Si-alkoxy groups and each R is a nonfunctional monovalent hydrocarbon group, a+b is from 1.0 to 3.0 and each molecule of uncured silicone resin contains an average of at least two groups R*, and (B) a silanol or hydrolysable compound of the formula where each R' represents a hydroxyl group or a hydrolysable group; each R" represents hydrogen, a monovalent hydrocarbon which optionally is substituted, or a group within the above definition of R'; and Ar is a substantially nonflexible linkage including at least one para-arylene moiety, so that the groups (R')$_2$R"Si— are spatially separated, wheein (A) and (B) are present in amounts to have a weight ratio of (A) to (B) of 5:1 to 20:1; in a solvent; casting the resulting solution in a mould; removing the solvent; and curing the composition in the mould.

21. A method according to claim 20, wherein the uncured silicone resin (A) has the empirical formula $(R^*)_a(R)_b SiO_{(4-a-b)/2}$ where a+b is between 0.8 and 1.6.

* * * * *